United States Patent [19]

Takayama et al.

[11] Patent Number: 5,041,427
[45] Date of Patent: Aug. 20, 1991

[54] LIPID A DERIVATIVES

[75] Inventors: Kuni K. Takayama; Nilofer Qureshi, both of Madison, Wis.

[73] Assignee: Wisconsin Alumni Research Foundation, Madison, Wis.

[21] Appl. No.: 467,449

[22] Filed: Jan. 19, 1990

Related U.S. Application Data

[63] Continuation-in-part of Ser. No. 383,832, Jul. 21, 1989.

[51] Int. Cl.$^5$ ..................... A61K 31/00; C07H 21/00; C07H 13/00; C07H 5/00
[52] U.S. Cl. ........................................ 514/53; 514/62; 536/22; 536/115; 536/116; 536/117; 536/119; 536/120; 536/53; 536/55; 536/18.7
[58] Field of Search ............................. 514/53, 62, 25; 536/117, 115, 116, 119, 22, 120, 18.7, 53, 55; 435/72, 74, 84, 85, 100, 131

[56] References Cited

U.S. PATENT DOCUMENTS 4,746,742  5/1988  Hasegawa et al. .................. 536/117

OTHER PUBLICATIONS

*Eur. J. Biochem.*, 180. 519–526 (1989), "Structural Analysis of the Nontoxic Lipid A of Rhodobacter Capsulatus 37b4", Jurgen H. Krauss et al.
Imoto, M., S. Kusumoto, T. Shiba, E. Th. Rietschel, C. Galanos, and O. Luderitz, 1985, Chemical Structure of *Escherichia coli* lipid A., Tetrahedron Lett. 26: 907–908.
Qureshi, N., K. Takayama, P. Mascagni, J. Honovich, R. Wong, and R. J. Cotter, 1988. Complete Structural Determination of Lipopolysaccharide Obtained from Deep Rough Mutant of *Escherichia coli.*, Purification by High Performance Liquid Chromatography and Direct Analysis by Plasma Desorption Mass Spectrometry., J. Biol. Chem. 263: 11971–11976.
Salimath, P. V., R. N. Tharanathan, J. Weckesser, and H. Mayer, 1983, Structural Studies on the Non-Toxic Lipid A from *Rhodopseudomonas sphaeroides* ATCC 17023., Eur J. Biochem, 136: 195–200.
Salimath, P. V., R. N. Tharanathan, J. Weckesser, and H. Mayer, 1984, The Structure of the Polysaccharide Moiety of *Rhodopseudomonas sphaeroides,* ATCC 17023 Lipopolysaccharide, Eur. J. Biochem, 144: 227–232.
Chemical Abstract, vol. 97, No. 11, 1982, Van Boeckel et al., "Chemical Synthesis of Diphosphorylated Lipid A Derivatives", the Abstract No. 92667b, Tetrahedron Lett. 1982, 23 (18), 1951–54 (Eng).
Chemical Abstract, vol. 100, No. 15, 1984, Van Boeckel et al., "Synthesis of Two Diphosphorylated Lipid A Derivatives Containing Alpha or Beta-Anomeric Phosphates", the Abstract No. 121493e, Recl.: J. R. Neth. Chem. Soc. 1983, 102 (10), 438–49 (Eng).
Strittmatter et al., "Nontoxic Lipopolysaccharide from *Rhodopseudomonas sphaeroides,* ATCC 17023," Journal of Bacteriology, Jul. 1983, pp. 153–158.
Cotter et al., "Structural Determination of Lipid A from Gram Negative Bacteria Using Laser Desorption Mass Spectrometry," Biomedical and Environmental Mass Spectrometry, vol. 14, pp. 591–598 (1987).
Takayama et al., "Diphosphoryl Lipid A from *Rhodopseudomonas sphaeroides,* ATCC 17023", Blocks Induction of Cachectin in Macrophages by Lipopolysaccharide, Infection and Immunity, Apr. 1989, pp. 1336–1338.

*Primary Examiner*—Ronald W. Griffin
*Assistant Examiner*—Everett White
*Attorney, Agent, or Firm*—Quarles & Brady

[57] ABSTRACT

Compounds are disclosed which are useful in a method of treating animals to protect them from the toxic effects of Gram negative endotoxin. They include the diphosphoryl lipid A (DPLA) which can be obtained from *R. sphaeroides* ATCC 17023 grown at about 26° C.

3 Claims, No Drawings

LIPID A DERIVATIVES

RELATED CASE

This application is a continuation-in-part of U.S. patent application Ser. No. 07/383,832 filed July 21, 1989.

TECHNICAL FIELD

This invention relates to novel compounds useful in a method of treatment of mammals to prevent clinical complications and death arising from septicemia or the presence of Gram-negative endotoxin (lipopolysaccharide) (LPS) in their bodies. More particularly, it relates to novel lipid A derivatives.

BACKGROUND ART

Lipopolysaccharide is a major constituent of the outer membranes of Gram negative bacteria. Studies have shown that it has the following three structural regions: 1) the O-specific polysaccharide; 2) the common core region; and 3) a lipid component called lipid A.

LPS is known to trigger many pathophysiological events in mammals, either when it is injected or when it accumulates due to Gram-negative infection. In general, the hydrophobic lipid A moiety is responsible for these pathophysiological effects which include B-lymphocyte mitogenesis, macrophage activation, interferon production, tumor regression, peripheral vascular collapse ("endotoxic" shock), pulmonary hypertension, pulmonary edema, disseminated intravascular coagulopathy and pyrogenicity.

It is known that a monosaccharide precursor lipid X has some activity in stimulating 70Z/3 cells and that a large excess of lipid X will compete with lipid A, partially blocking its toxic effects[13]. It is also known that monophosphoryl lipid A from *E. coli* has numerous biological activities associated with LPS, but its toxicity is attenuated[25]. On the other hand, diacyldiphosphoryl lipid A from *E. coli* is known to have very low or no biological activities associated with LPS and it has moderate antagonistic activity against the activation of 70Z/3 cells by LPS (Kirkland and Takayama, unpublished data). It also is known that diphosphoryl lipid A from *E. coli* and Salmonella strains are highly toxic[25].

The LPS obtained from *R. sphaeroides* ATCC 17023 grown at 30° C. was reported to be non-toxic by Strittmatter et. al.[21] The complete structure of the LPS from this source has now been established[14,18,19]. The structure of the lipid A moiety of the LPS from *R. sphaeroides* is strikingly similar to the lipid A of the toxic enterobacterial and Salmonella LPS[9,22]. The two major differences noted are the presence of a 3-ketotetradecanoate instead of a 3-hydroxytetradecanoate at the 2'-position ($R_4$) and a $\Delta^7$-tetradecanoate instead of a tetradecanoate in acyloxyacyl linkage at the 2'-position ($R_2$) of the glucosamine disaccharide of the *R. sphaeroides* lipid A. See Formula II for the diphosphoryl lipid A (DPLA) from *R. sphaeroides*.

Another nontoxic LPS from *Rhodopsuedomonas capsulata* ATCC 23782 was reported by Omar et al[27]. The lipid A from the LPS of this source has been prepared and its complete structure determined. This lipid A has 3-ketotetradecanoate at both 2- and 2'-positions ($R_2$ and $R_4$) of the glucosamine disaccharide, a 3-hydroxytetradecanoate at the 3'-position ($R_3$), and $\Delta^9$-dodecanoyloxydecanoate at the 3'-position ($R_1$) (See Formula III for the structure of the DPLA from *R. capsulata*.)

There is a need for improved compounds for protecting animals from the detrimental effects of gram-negative endotoxins.

BRIEF SUMMARY OF THE INVENTION

It is the primary object of the present invention to disclose novel compounds useful in a method of protecting mammals from the detrimental effects of Gram-negative endotoxins.

The novel compounds of the present invention which are useful in a method of treating a mammal to protect it from the detrimental effects of Gram-negative endotoxins are derivatives of lipid A having the following formula:

FORMULA I

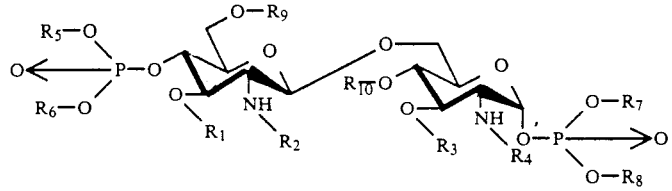

in which $R_1$, $R_2$, $R_3$ and $R_4$ are selected from hydrogen,

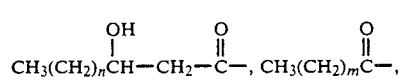

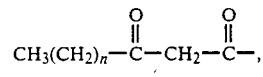

alkyl branched or 2-hydroxy fatty acyl group wherein n is 1 to 14 and m is 2 to 16. The above groups can occur in various combinations.

The substituents on the phosphates ($R_5$, $R_6$, $R_7$, and $R_8$) can be H, lower alkyls of $C_1$ to $C_6$, an aryl, such as phenyl, naphthyl or the like, an acyl such as

in which R is an alkyl of 1 to 6 carbon atoms or polar head groups such as aminoarabinose, phosphorylethanolamine or any other basic group that does not interfere with or detract from the desired properties. In addition, the phosphate group at the 4'-position can be cyclized with the hydroxyl group of the 6′-position ($R_9$).

The substitution at the 4- and 6′-positions ($R_{10}$ and $R_9$) can be a $C_1$ to $C_{16}$ alkyl group in an ether linkage, a $C_2$ to $C_{18}$ fatty acyl group in an ester linkage, or a straight or branched glycosidic residue from 1–20 glycosidic units per residue (preferably at $R_9$).

Monophosphoryl lipid A (MPLA) and DPLA are expected to be useful with the DPLA being preferred. In the MPLA, the phosphate group can be either at the 1- or the 4′-position. The diacyl, triacyl, tetraacyl, pentaacyl, hexaacyl, and heptaacyl DPLA are all expected to be useful with the pentaacyl DPLA being preferred. Either the monosaccharide (lipid X analog) or the disaccharide of lipid A are expected to be useful with the disaccharide being preferred.

The glycosidic units can be glycopyranosyl or glycofuranosyl, as well as their amino sugar derivatives. The residues may be homopolymers, random, or alternating or block copolymers thereof. The glycosidic units have free hydroxy groups, or acylated hydroxy groups.

The glycosides can comprise up to 20 glycosidic units. Preferred, however, are those having less than 10. Most preferred are those having 3 or less than 3 glycosidic units. Specific examples are those containing 1 or 10 glycosidic units in the glycoside residue.

Among the possible glycopyranosyl structures are glucose, mannose, galactose, gulose, allose, altrose, idose, or talose. Among the furanosyl structures, the preferred ones are those derived from fructose, arabinose or xylose. Among preferred diglycosides are sucrose, cellobiose, maltose, lactose, trehalose, gentiobiose, and melibiose. Among the triglycosides, the preferred ones may be raffinose or gentianose. Among the amino derivatives are N-acetyl-D-galactosamine, N-acetyl-D-glucosamine, N-acetyl-D-mannosamine, N-acetylneuraminic acid, D-glucosamine, lyxosylamine, D-galactosamine, and the like.

The glycosidic derivatives of the compounds of the present invention as well as the other lipid A derivatives can be prepared by standard synthetic methods well known to those skilled in the art.

The compounds of the present invention are useful in a method of protecting a mammal from the detrimental effects of Gram-negative endotoxin which comprises administering to the mammal, preferably by injection, a safe and effective amount of a compound of Formula I. In addition, the purified nontoxic LPS from *R. sphaeroides* and *R. capsulata* can afford protection against gram-negative endotoxin.

The two preferred compounds are the pentaacyl DPLAs obtained from the LPS of *R. sphaeroides* and *R. capsulata*. They are the following:

1. O-[2-amino-2-deoxy-$N^2$-(3-ketotetradecanoyl),$O^3$-(3-hydroxydecanoyl)-β-D-glucopyranosyl]-(1→6)-2-amino-2-deoxy-$N^2$-($\Delta^7$-tetradecanoyl-3-oxytetradecanoyl),$O^3$-(3-hydroxydecanoyl)- -D-glucopyranose 1,4′-bisphosphate.

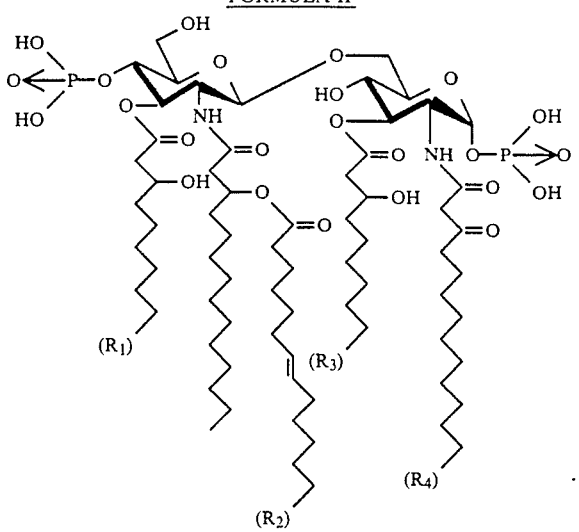

FORMULA II

2. O-[2-amino-2-deoxy-$N^2$-(3-ketotetradecanoyl),$O^3$-(3-hydroxydecanoyl)-β-D-glucopyranosyl]-(1→6)-2-amino-2-deoxy-$N^2$-(3-ketotetradecanoyl),$O^3$-($\Delta^9$-dodecenoyl-3-oxydecanoyl)- -D-glycopyranose 1,4,-bisphosphate.

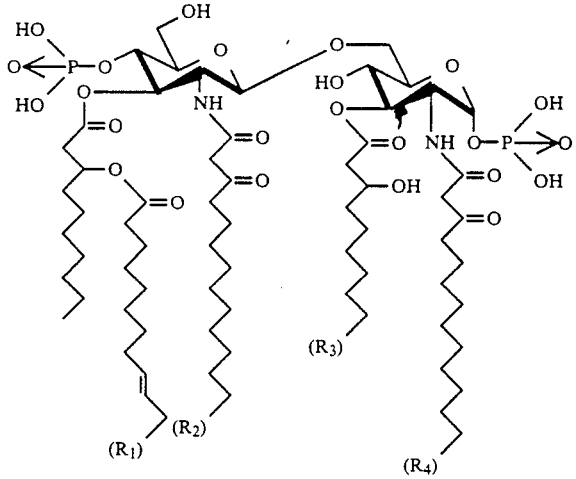

FORMULA III

Other compounds represented by Formula I include the following

1. Monophosphoryl lipid A (MPLA).
2. Lipid X analog.
3. Tetraacyl, hexaacyl, and heptaacyl derivatives of lipid A. This includes the analog of precursor IVA. All of the above compounds may contain the 3-keto fatty acyl group at either/both 2- and 2′-position(s) of the sugar. A 3hydroxy fatty acyl groups equal to or less than $C_{12}$ at the 3 and 3′ positions and possibly a double bond in the fatty acyl group at the 2′- and/or 3′-position. The purified LPS from *R. sphaeroides* and *R. capsulata* can also be used.

Methods of Preparation

1. The MPLA can be prepared from the LPS by hydrolysis in 0.1 N HCl at 100° C. for 30–60 min, followed by purification on either silicic acid or DEAE cellulose column.

2. A single fatty acid can be removed from a heptaacyl, hexaacyl or pentaacyl lipid A by hydrolysis in 0.033% (v/v) triethylamine at 100° C. to yield the corresponding hexaacyl, pentaacyl, and tetraacyl products, respectively.

3. All ester-linked fatty acids can be removed by deacylation reaction in 0.1 M NaOH to yield the diacyl lipid A. Since the 3-ketotetradecanoate groups are N-linked, they will survive this hydrolysis.

4. Other unusual disaccharide lipid A's listed can be synthesized by the methods disclosed by Shiba et al.[34]. The introduction of a keto fatty acid may pose a special synthetic problem.

5. The lipid X analogs can be synthesized by well established procedures. The introduction of a keto fatty acid may pose a special synthetic problem.

DESCRIPTION OF PREFERRED EMBODIMENT

The preferred compound DPLA can be prepared from the LPS of R. sphaeroides, having the identifying characteristics of the strain ATCC 17023, which has been grown at about 26° C.

In the preferred method the R. sphaeroides is grown photoheterotrophically in medium 550 (ATCC) at 26° C. (12-14 days) as previously described[14] and harvested by using a cell concentrator and centrifugation. For the extraction of the contaminating and unwanted pigments, 700 g of cell paste are extracted with stirring overnight at 22° C. with 4 liters of ethanol/n-butanol (3:1). This extraction is repeated twice, then the cell paste is extracted once with 4 liters each of absolute ethanol, acetone and diethyl ether. The dry weight of the extracted light brown cells is 70.4 g. The LPS is extracted from 70.4 g of the light brown cells to yield 640 mg (0.9%). This LPS preparation is suspended in 0.1 M EDTA, pH 7.0 (at 1.0 mg/ml) and sonicated for 10 minutes as described by Qureshi et al.[15] This suspension is stirred at 22° C. for 3 hours. The disaggregated LPS is recovered by extraction with chloroform/methanol to yield 310 mg of LPS.

The LPS is finally purified by the use of the reverse-phase SepPak cartridge (Waters Associates, Inc., Milford, Mass.). The cartridge is first washed with 10 ml of methanol. The LPS (30 mg) is loaded on a cartridge in 250 μl of chloroform/methanol (4:1) and washed successively with 10 ml of methanol, 20 ml of acetonitrile, and 20 ml of chloroform/methanol (4:1). The purified LPS is obtained from the last wash (25.7 mg, 86%).

The crude LPS (900 mg) is hydrolyzed in 0.02 M sodium acetate, pH 2.5 at 2 mg/ml and incubated at 100° C. for 70 minutes to yield a mixture of monophosphoryl lipid A and several forms of DPLA's. The resulting DPLA product may be recovered by extracting with chloroform/methanol as previously described.[14] The DPLA can be purified by preparative thin layer chromatography on silica gel H (500 μm) at a load of 4 mg/20×20 cm plate using the solvent system of chloroform/methanol/water concentrated ammonium hydroxide (50:25:4:2). The DPLA band is visualized with iodine vapor and recovered from the silica gel by extraction with chloroform/methanol/water (66:33:4).

The mixture of monophosphoryl lipid A and the several forms of DPLA's can also be fractionated on a DEAE-cellulose column to yield the desired pentaacyl DPLA in highly purified form. The mixture (140 mg) is applied to a 3.5×29 cm column in the acetate form and the column is washed with 250 ml of chloroform/methanol/water (2:3:1). A linear gradient of 0.03 to 0.08 M ammonium acetate in chloroform/methanol/water (2:3:1) is used to fractionate the DPLA. One hundred fifty fractions (13 ml) are collected and analyzed by spot charring to locate the DPLA. These fractions are analyzed by thin layer chromatography using silica gel H and the solvent system of chloroform/pyridine/formic acid/water (40:48:12:4). Specific fractions are pooled and desalted in a two-phase chloroform/methanol/water solvent. Peak A, fractions 14-19, contains the monophosphoryl lipid A (11.9 mg), Peak B, fractions 52-61, (11.9 mg) contains an unidentified form of DPLA and Peak C, fractions 68-90, contains the purified pentaacyl/DPLA (42.9 mg). Alternatively, DPLA can be fractionated using a silicic acid column and the solvent system of chloroform/pyridine/formic acid/water. Peak B might also be useful in treating a mammal to protect it from the detrimental effects of the Gram negative endotoxin.

The DPLA thus obtained was unable to induce interleukin-1 release in murine peritoneal macrophage and blocked this activity by toxic deep rough chemotype LPS. These results along with the previously reported results on the tumor necrosis factor assay strongly suggests that the pentaacyl DPLA from R. sphaeroides lacks endotoxic activity and yet it is an effective antagonist of LPS-induced activation of macrophage.

Examples 1 and 2 describe a simple procedure for the preparation of highly purified pentaacyl DPLA from the LPS of R. sphaeroides. The DPLA was characterized by the combined reverse-phase HPLC and mass spectral analyses. It was found to antagonize the induction of IL-1 release by toxic Re LPS in murine macrophage. This indicated that the R. sphaeroides DPLA is not endotoxic.

EXAMPLE 1

Growth of Bacteria and Preparation of Lipopolysaccharide

R. sphaeroides ATCC 17023 was grown photoheterotrophically in medium 550 as previously described[14]. Cells were grown at 26° C. (12-14 days) and harvested by using a cell concentrator and by centrifugation. The cell paste (700 g) was extracted with stirring overnight at 22° C. with 4-1 of ethanol/n-butanol (3:1 v/v). This was repeated several times until all the pigments were removed. This was followed by extraction once with 4-1 of ethanol, twice with 3-1 of acetone and once with 4-1 of diethyl ether. LPS was extracted from 70.4 g of pigment-depleted cells using the method as described by Qureshi et al.,[34] yielding 640 mg of the LPS.

EXAMPLE 2

Preparation of the DPLA

The LPS (640 mg) obtained from R. sphaeroides was suspended in 0.02M sodium acetate, pH 2.5 at 3 mg/ml incubated for 70 min at 100° C. and centrifuged at 8,000×g for 10 min. The pellet was dissolved in 60 ml of chloroform/methanol (2:1, v/v); 24 ml of water were added and then mixed. After standing the lower layer was recovered as previously described[15] to yield 240 mg of crude DPLA.

The crude DPLA (140 mg) was dissolved in 20 ml of chloroform/methanol (2:1, v/v) applied to a 3.5×29 cm DEAE-cellulose column (in acetate form), and the column was washed with 250 ml of chloroform/methanol/water (2:3:1, v/v). DPLA was eluted from the column using a linear gradient of 0.03-0.08M ammonium acetate in chloroform/methanol/water (2:3:1, v/v). One hundred and fifty 13 ml fractions were collected and analyzed for total phosphorous and the appearance of char-positive spots on a silica gel thin layer plate. Fractions giving char positive spots were analyzed by TLC using silica gel H plate and a solvent system of chloroform/pyridine/formic acid/water (10:12:3:1, v/v). Fractions containing the single TLC component were pooled and desalted in a two phase chloroform/methanol/water system as described previously [15]. The following pooled fractions were obtained. Peak A (14-19, 11.9 mg) containing the monophosphoryl lipid A (Rf=0.75 in the chloroform/pyridine/formic acid/water system mentioned above), Peak B (52-61, 11.9 mg) containing an unidentified form of DPLA (Rf=0.20) and peak C (67-87, 28.2 mg) containing the desired DPLA (Rf=0.59). Peak C represented the nontoxic highly purified pentaacyl DPLA.

For structural analysis the pentaacyl DPLA was converted to the free acid by passage through a Chelex 100 (Na+) and DOWEX 50 (H+) double layer column in chloroform/methanol (4:1, v/v), methylated with diazomethane as described previously[35] and fractionated by HPLC.

HPLC fractionation

A 8 mm×10 cm Nova-Pak cartridge ($C_{18}$-bonded, end-capped 5μ silica, Waters Associates, Inc.) was used at a flow rate of 2 ml/min. For the fractionation of the *R. sphaeroides* tetramethyl DPLA, a linear gradient of 20-80% isopropanol in acetonitrile was used over a period of 60 min.

Mass Spectrometry

Plasma desorption mass spectra were obtained on a BIO-ION Nordic (Uppsala, Sweden), BIN-10K plasma desorption time-of-flight mass spectrometer equipped with a PDP 11/73-based data system. Purified DPLA was dissolved in chloroform/methanol (4:1, v/v) solution and electrosprayed onto a mylar backed aluminium foil. Positive ion mass spectra were recorded with an accelerating potential of 16 KV for 3 to 9 million primary events with resolution of 1 n sec/channel. H+ and Na+ were used for calebration.

FAB (fast atom bombardment) mass spectra were obtained on a Kratos (Manchester, England) MS-50 high resolution, double focussing mass spectrometer equipped with an Ion Tech (Teddington, England) saddle field atom gun. Samples were desorbed from the monothioglycerol matrix by a beam of 8 Kev Xe atoms. Positive ion spectra were recorded with an accelerating potential at 8 KV over the mass range of 2200-350 at a rate of 30 se/decade.

IL-1 assay

Peritoneal exudate cells were harvested from $BDF_1$ mice 48 h after an intraperitoneal injection of thioglycollate. Elicited macrophages were obtained as previously described[36]. Macrophages were either pretreated with *R. sphaeroides* DPLA (0.1-10 μg/ml) followed by the addition of toxic Re LPS (0.1 μg) after 2 h, or immediately stimulated with Re LPS (0.01-1.00 μg/ml). Control wells were treated with 10 μl of media containing 0.5% triethylamine. Cultures were incubated at 37° C. in the presence of 5% $CO_2$ for 18 h at which time the supernatants were collected and frozen at −20° C. until assayed. IL-1 activity was determined by the comitogenic thymocyte assay.[25]

EXAMPLE 3

Effects of Pentaacyl DPLA on the Induction of IL-1 in Murine Macrophages

Pentaacyl DPLA from *R. sphaeroides* tested at 0.1, 1.0, and 10 μg/ml was unable to induce IL-1 in murine peritoneal macrophages. This compares with the toxic Re LPS which gave maximum induction at 0.1 μg/ml. In the blocking experiment 0.1, 1.0, or 10.0 μg/ml of pentaacyl DPLA was added to the cells 2h prior to adding 0.1 μg/ml of the Re LPS. The addition of 1.0 μg/ml of pentaacyl DPLA (DPLA to Re LPS mass ratio of 10:1) caused a 60% inhibition of induction of IL-1 release. When this ratio was increased to 100:1, the inhibition was total.

The pentaacyl DPLA from the LPS of *R. sphaeroides* is the first lipid A structure found to show no endotoxic activity and yet to be an effective antagonist of LPS induced activation of macrophages and B cells. This DPLA appears to compete favorably with toxic LPS for the active LPS/lipid A binding sites. For this reason, it can be a useful reagent to study the receptor-LPS interaction.

The LPS, MPLA and DPLA of *R. capsulata* may be prepared as follows.

*R. capsulata* H. Gest strain St Louis (ATCC 23782) is grown photoheterotrophically in medium 550 at 26° C. for 12 days and harvested by using the cell concentrator and centrifugation. The cell paste (598 g) is extracted successively with stirring at 22° C. with 4 l of ethanol/butanol (3:1) for 2 h, the same solvent overnight, and acetone twice for 2 h. The crude cell wall is prepared by suspending 50 g of the acetone-dried cells in 100 ml of 0.01 M potassium phospate buffer, pH 7.0. A French pressure cell is used to rupture the cells. The cells are centrifuged at 10,000×g for 30 min and the pellet is resuspended in 100 ml of the buffer by homogenizing. The suspension is centrifuged at 10,000×g and the pellet is recovered. This procedure is repeated twice and the pellet is finally washed with water and lyophilized to yield 14.5 g of crude cell wall.

The LPS is extracted from the cell wall preparation using a modified procedure of the hot phenol-water extraction[28]. The cell wall preparation (14.5 g) is suspended in 160 ml of water, sonicated for 10 min and heated to 68° C. Phenol (160 ml) is added to the suspension and stirred at 68° C. for 30 min. Then it is cooled to 4° C. and centrifuged at 10,000×g for 30 min. The phenol layer (lower layer) is recovered. This procedure is repeated twice with the cell wall pellet. All three phenol extracts are pooled and dialyzed against running tap water for 2 days. The impurities that precipitate out are filtered out with cheese cloth. The supernatant is again dialyzed against running water and finally with distilled water for 3 days. The dialyzed phenol layer which contains the LPS is lyophilized to yield 610 mg. The preparation of the MPLA and DPLA from the LPS of *R.capsulata* is identical to that described from the LPS of *R. sphaeroides*.

Comparative Tests

To demonstrate the biological activity of the DPLA comparative studies were run in which the DPLA prepared from the LPS of *R. sphaeroides* was chosen to be the antagonist, because it is easily obtained in a highly purified form and it is similar to the toxic DPLA from the LPS of *Salmonella typhimurium*[25]. It was characterized as the tetramethyl derivative by plasma desorption mass spectrometry. It is nontoxic based on the chick embryo lethality test ($CELD_{50} > 20$ μg).

For the antagonist to activate the RAW 264.7 murine macrophage cell line, we chose the toxic deep rough chemotype LPS (ReLPS) from *Escherichia coli* D31m4, which was recently purified and characterized[15]. We found that the DPLA from *R. sphaeroides* blocks the induction of cachectin (tumor necrosis factor, TNF) by the RAW 264.7 cells. This is a clear example of a lipid A derivative showing strong antagonism against a toxic agonist in the induction of cachectin.

The immunoblot method was used to quantitate the cachectin/TNF production by RAW 264.7 murine macrophage cells. RAW 264.7 cells[4,16] were seeded in 24-well plates (Nunc) at a density of $3 \times 10^5$ cells/well in Dulbecco's modified Eagle's medium supplemented with 5 percent fetal calf serum. After 12 hours, cell monolayers were washed twice with 1 ml of serum-free medium and then left covered with 2 μl of the same. An aqueous suspension of DPLA and/or ReLPS was then added to a final concentration indicated. Cells were incubated for 12 hours, after which the medium was removed for measurement of TNF by immunoblotting. One hundred μl of medium was mixed with 100 μl of SDS-containing sample buffer, heated to 100° C. for 5 minutes, and subjected to electrophoresis in a 10–15% polyacrylamide gradient gel. Proteins were then transferred to nitrocellulose electrophoretically, and TNF was visualized through the use of a rabbit anti-mouse TNF polyclonal serum[3,5] applied at a 1:100 dilution, followed by alkaline phosphatase-conjugated goat anti-rabbit IgG (Bio-Rad).

An immunoblot of cachectin/TNF produced by RAW 264.7 murine macrophage cells, showed induction by toxic ReLPS, lack of induction by DPLA (*R. sphaeroides*), and blocking of induction by the DPLA. Bands were visualized using nitroblue tetrazolium. Approximately 0.1 ng of cachectin/TNF may be detected as a band. The antiserum also recognized the processing intermediates (prohormones) on Western blot.

The immunoblot showed that the toxic ReLPS from *E. coli* caused the induction of cachectin by RAW 264.7 cells at all concentrations tested (1–100 ng/ml). Optimal induction occurred at 10 ng/ml of ReLPS. The DPLA of *R. sphaeroides* was not able to induce the formation of cachectin at 1–1000 ng/ml. We observed only slight induction at $10^4$ ng/ml. When DPLA of *R. sphaeroides* was added together with 10 ng/ml of ReLPS, we observed definite inhibition in the induction at $10^3$ ng/ml of DPLA (ReLPS to DPLA mass ratio of 1:100). This inhibition was probably maximal at $<10^4$ ng/ml (ratio of $1:<10^3$). Other lipid A analogs and precursors related to the toxic LPS, including monophosphoryl lipid A[23,25], lipid X[24], and precursor IVA[20] caused the induction of cachectin in RAW cells when analyzed by the immunoblot method and were not appropriate to use as inhibitors.

When the DPLA was analyzed for TNF production by RAW 264.7 cells using the indicator cell line L929, it also showed that the DPLA is not effective in the induction of TNF.

Table I shows that there is induction of TNF (cachectin) by ReLPS, lack of induction by DPLA and blocking of induction by pretreatment with DPLA using RAW 264.7 cells and indicator cell line L929.

TABLE I

| ReLPS(ng/ml) | 0.1 | 1.0 | 10 | 100 |
|---|---|---|---|---|
| Dilution to get 50% killing | 64 | 1440 | 1522 | 2344 |
| DPLA 10,000 (ng/ml) | | 10 | 100 | 1000 |
| Dilution to get 50% killing | 0 | 0 | 71 | 346 |
| DPLA 10,000 (ng/ml) | | 10 | 100 | 1000 |
| ReLPS (ng/ml) | 1.0 | 1.0 | 1.0 | 1.0 |
| Dilution to get 50% killing | 829 | 112 | 86 | 234 |
| % inhibition | 43 | 92 | 94 | 84 |

The RAW 264.2 macrophage tumor cell line was used. The TNF unit is derived by determining how far one can dilute the supernatant of the culture to achieve 50% killing of an indicator cell line.

The DPLA was added to the culture of RAW 264.2 2 hours before exposure to the ReLPS.

Interleukin-1 (IL-1) is another important mediator of lethality in Gram-negative sepsis. Competitive experiments similar to TNF assay were carried out in the induction of IL-1 using peritoneal macrophage. Peritoneal exudate cells were harvested from $BDF_1$ mice 48 h after an intraperitoneal injection of thioglycollate as described previously (Lederer and Czuprynki). Macrophages were either pretreated with *R. sphaeroides* DPLA (0.1–10 μg/ml) followed by addition of toxic ReLPS (0.1 μg), or immediately stimulated with ReLPS (0.01–1.00 μg/ml). Control wells were treated with 10 μl of media with 0.5% triethylamine. Cultures were incubated at 37° C. in the presence of 5% $CO_2$ for 18 h at which time the supernatants were collected and frozen at $-20°$ C. until assayed. IL-1 activity was determined by the previously described comitogenic thymocyte assay (Meltzer, 1981).

Purified DPLA from *R. sphaeroides* had no IL-1/releasing activity (see Table II). However, it blocked the release of IL-1 in peritoneal macrophages by ReLPS from *E. coli* in a concentration dependent manner. The ReLPS to DPLA mass ratios of 1:10 and 1:100 (when 0.1 μg of ReLPS was used) gave 60 and 100% inhibitions, respectively. These results further support the notion that the inhibition is due to the competitive binding by *R. sphaeroides* DPLA for the active sites on the macrophages.

TABLE II

Inhibition by *R. sphaeroides* DPLA of induction of IL-1 in thioglycollate-elicited peritoneal macrophages by toxic ReLPS

| E. coli ReLPS (μg/ml) | R. spaeroides DPLA (μg/ml) | Measure of IL-1 induction | | % Inhibition |
|---|---|---|---|---|
| | | CPM | CPM - Blank | |
| 1.0 | — | 43,353 (6657) | 35,565 | — |
| 0.1 | — | 58,565 (2432) | 50,777 | — |
| 0.01 | — | 13,610 (5212) | 5,822 | — |
| — | 10.0 | 3,764 (785) | 0 | — |
| — | 1.0 | 2,911 (383) | 0 | — |
| — | 0.1 | 3,511 (616) | 0 | — |
| 0.1 | 10.0 | 5,892 (886) | 0 | 100 |
| 0.1 | 1.0 | 28,276 (4860) | 20,491 | 60 |
| 0.1 | 0.1 | 51,999 (4860) | 44,211 | 13 |

ReLPS was added to the culture 2 h after adding the *R. sphaeroides* DPLA. The triethylamine-medium blank was 7,788 (238). Standard deviation in CPM are given in parentheses.

At the very high concentration of DPLA of $10^4$ ng/ml, we did observe a measurable but low level in the induction of TNF. This confirms the results obtained by the immunoblot method. In the competition experiment, when 100 ng/ml of DPLA was added 2 hours before adding 1.0 ng/ml of the toxic ReLPS to the macrophage culture, it gave a 95 percent inhibition in the induction of TNF by ReLPS (ReLPS to DPLA mass ratio of 1:100). Even when only 10 ng/ml of DPLA was used in a similar experiment, 55 percent inhibition was observed (ReLPS to DPLA ratio of 1:10). When this ratio was increased to $1:10^4$, the inhibition was lowered to 81 percent. This could be due to the ability of DPLA alone to induce TNF production at very high concentrations.

TABLE III

| Treatment (ng/ml) | Dilution for 50% killing | Inhibition % |
|---|---|---|
| ReLPS | | |
| 0.1 | 180 | — |
| 1 | 5057 | — |
| 10 | 6272 | — |
| 100 | 8978 | — |
| DPLA | | |
| 10 | <10 | — |
| 100 | 19 | — |
| 1000 | 201 | — |
| 10000 | 764 | — |
| ReLPS (1.0 ng/ml) + DPLA | | |
| 10 | 2287 | 55 |
| 100 | 269 | 95 |
| 1000 | 201 | 96 |
| 10000 | 973 | 81 |

TNF unit was derived by determining dilution of culture supernatant that kills 50 percent of the indicator cell line.

DPLA was added 2 hours before exposing culture to ReLPS. The ReLPS and DPLA were complexed with bovine serum albumin.[1]

The compound DPLA was also shown to be inactive in the activations of 70Z/3 cells by toxic LPS. Table IV shows the effect of pretreatment of 70Z/3 cells with DPLA on their activation by ReLPS.

TABLE IV

| ReLPS (μg/ml) | 0.003 | 0.01 | 0.1 | 0.3 |
|---|---|---|---|---|
| Activation[1] (% fluorescence) | 20.5 | 41 | 69 | 71.5 |
| DPLA (μg/ml) | 0.1 | 0.3 | 1.0 | 3.0 |
| ReLPS(μg/ml) | 0.1 | 0.1 | 0.1 | 0.1 |
| Activation[1] (% fluorescence) | 52 | 45 | 26.5 | 14 |
| % inhibition | 25 | 35 | 62 | 80 |

[1]Corrected for background of 5% fluorescence.
[2]The DPLA stimulated 70Z/3 pre-B cells to the extent of from 2.5-6.0% fluorescence at concentrations of 1.0-10 mg/ml. In the competitive inhibition experiment, the cells were first exposed to DPLA for 2 hours before adding the ReLPS. In all experiments, the ReLPS and DPLA were complexed with bovine serum albumin.

1. Corrected for background of 5% fluorescence.
2. The DPLA stimulated 70Z/3 pre-B cells to the extent of from 2.5-6.0% fluorescence at concentrations of 1.0-10 mg/ml. In the competitive inhibition experiment, the cells were first exposed to DPLA for 2 hours before adding the ReLPS. In all experiments, the ReLPS and DPLA were complexed with bovine serum albumin.

Table V shows the effect of concentration of ReLPS and DPLA on the activation of 70Z/3 cells.

TABLE V

| ReLPS(μg/ml) | DPLA (μg/ml) | | |
|---|---|---|---|
| | 0 | 1.0 | 3.0 |
| | Activation (% fluorescence)[1] | | |
| 0 | 0 | 3.5 | 2.56 |
| 0.1 | 73 | 28.5(61) | 13.5(92) | 4.5(94) |
| 0.3 | 74 | 48.5(34) | 30(59) | 11(85) |
| 1.0 | 75 | 57.5(22) | 55(26) | 25(66) |
| 10' | 76 | 75.5(0.5) | 77(0) | 69(9) |

[1]The % inhibition is indicated in parentheses.

Table VI shows the effect of the addition of DPLA prior to or after the addition of ReLPS on the inhibition of activation of 70Z/3 cells.

TABLE VI

| Time of addition of[1] DPLA (hour) | Activation (% fluorescence) | % inhibition |
|---|---|---|
| −2 | 11 | 85 |
| 0 | 10.5 | 86 |
| 2 | 20 | 73 |
| 4 | 24 | 67 |
| 6 | 24.5 | 66 |
| 8 | 9.5 | 60 |
| 16 | 44 | 40 |
| 20 | 54 | 26 |
| 24 | 55.5 | 24 |

In this experiment, 0.1 μg/ml of ReLPS and 3.0 μg/ml of DPLA were used.

[1]The time of pre/post treatment of 70Z/3 cells with DPLA relative to the time of addition of ReLPS are indicated.

These results clearly show that the DPLA is able to effectively antagonize the induction of TNF by toxic ReLPS in a dose-dependent manner in RAW 264.7 cells. We have also shown that DPLA is an effective antagonist in the LPS-induced activation of 70Z/3 pre-B cells. DPLA and the lipid A moeity of the toxic ReLPS are structurally very similar, which strongly suggests that they both compete for the same active binding sites on the macrophage. Thus DPLA which can be prepared rather easily in highly purified form, also is a useful reagent in studying the nature of the LPS/lipid A binding to macrophages and perhaps to other responding cells.

These results are consistent with previous biological studies done with other types of lipid A analogs and LPS derivatives. Lipid X and its analog 3-aza-lipid X have been found to inhibit the LPS-induced neutrophil priming[6]. It has been suggested that these analogs compete with LPS for cellular binding sites. The selective deacylation of the non-hydroxyl fatty acids from LPS has been shown to render the new product less toxic and effective in inhibiting the neutrophil-endothelial cell interaction induced by LPS[12]. The competitive interaction of LPS and the deacylated LPS for specific cell-surface or intra-cellular target has been implicated.

The possible kinetics of this inhibition is revealed in a study that shows that the continued presence of LPS is required for TNF production[8]. Removal of LPS at any time results in abrupt cessation of further TNF production. One might then expect abrupt cessation of further TNF production after adding sufficient amounts of DPLA.

The lipid A moiety of toxic LPS acting on the macrophage is believed to play a central role in mediating endotoxic reactions[7,11]. It has been suggested that cachectin (TNF) is the mediator of lethality in Gram-negative sepsis. This is supported by several recent studies that included the use of recombinant TNF to induce many of the deleterious effects of endotoxin[2,10,17,26] and polyclonal antibody in passive immunization against cachectin[5]. Thus, the formation of cachectin might be a suitable target for pharmacotherapeutic intervention, therefore, DPLA also can be a useful inhibitor in this regard. DPLA is more effective than lipid X in protecting mice against a lethal dose of endotoxin as reported in the literature[13].

It also appears, that the pretreatment of mammals, such as sheep or mice, with DPLA should make them immediately resistant to the lethal effects of injection of Gram-negative endotoxin. This apparent antagonism between DPLA and endotoxin should have useful applications in clinical situations and disease states that are caused by endotoxin, such as Gram negative sepsis following surgery in humans and animals, bovine or porcine mastitis, and other endotoxin-related veterinary diseases listed in Table VI.

The lethal dose of *E. coli* endotoxin was determined both for the intravenous and for the intraperitoneal challenge. The lethal dose that killed 100% of the mice ($LD_{100}$) was 250 μg intravenously and 500 μg intraperitoneally. (It is important to standardize each lot of endotoxin with each lot of mice.) To determine the approximate dose of lipid A derivative needed to protect against a lethal challenge of endotoxin, mice are pretreated with the lipid A derivative intraperitoneally 2 hours before challenge with 1500 μg of endotoxin, which is 3 times the $LD_{100}$ dose. Pretreatment of mice with the lipid A derivative appeared to prolong the time to death.

Although the diphospholipids from *E. coli* and Salmonella strains are highly toxic DPLA having the structure of the diphosphoryllipid A from *R. sphaeroides* is not. The $LD_{50}$ of DPLA in galactosamine-sensitized mice was greater than 20 mg/kg.

In contrast to treatment with the lipid A derivative (DPLA), a single injection of *E. coli* derived lipopolysaccharide (10–20 μg/kg) caused serious pulmonary hypertension, and after 15–30 minutes, an animal treated with the *E. coli* lipopolysaccharide began to tremble, cough and lay down. The symptoms became more severe over the next few hours and were accompanied by fever. About half the animals died by 24 hours.

Purified DPLA obtained from the nontoxic LPS of *R. sphaeroides* ATCC 17023 grown at about 26° C. was shown to block the induction of cachectin (TNF) in RAW 264.7 macrophage cell line by toxic deep rough chemotype LPS (ReLPS) of *E. coli* in a concentration-dependent manner. The ReLPS to DPLA mass ratios of 1:10 and 1:100 (when 1.0 ng/ml of ReLPS was used) gave 55 and 95 percent inhibitions respectively, in the induction of cachectin. Since the structure of the DPLA from *R. sphaeroides* is so similar to that of the lipid A moiety of the toxic ReLPS from *E. coli*, this inhibition is probably due to competitive binding by DPLA for the active sites on the macrophage. DPLA also should be a useful reagent to study the nature of LPS/lipid A binding in macrophage and perhaps other responding cells.

Implications for therapy

Previous work on the lethal endotoxicity of Gram-negative LPS demonstrates that limited prevention of the complications of injection of this material could be achieved through the administration of glucocorticoids, prostaglandins, naloxone, pressors, fluid replacement therapy or anti-LPS antibodies. In addition, all existing therapies against LPS lethality are dependent upon their being given prior to or very shortly after the administration of the LPS challenge.

The administration of a non-toxic lipid A derivative, such as DPLA, may ameliorate pathological conditions created by many of the endotoxin-induced diseases listed in Table VII. Furthermore, protection by the lipid A derivative may be obtainable even after endotoxin had been administered. This is an extremely important therapeutic consideration, since the signs and symptoms of a disease are almost always manifest before therapy is initiated. Although the mechanism(s) of protection by which the lipid A derivative is effective against LPS challenge remain unknown, the data fit best with competition for a common target molecule, such as membrane receptor(s) on endothelial or vascular cells.

Because lipid A derivatives having a 3-ketotetradecanoate instead of a 3-hydroxytetradecanoate at the 2 position and a $\Delta^7$-tetradecanoate instead of a tetradecanoate in acyloxyacyl linkage at the 2'-position of the glucosamine disaccharide of the LPS of *R. sphaeroides* grown at about 26° C. are not by themself toxic to animals, they may be useful for treatment of other diseases which LPS is known to ameliorate, but cannot be employed because of its toxicity. Thus, it might be anticipated that the lipid A derivatives would protect mammals from skatole toxicity, oxygen toxicity, and drugs that enhance the production of free radicals (e.g. bleomycin, nitrofurantoin, adriamycin, etc.). It is known that LPS stimulates the activity of various enzymes that protect animals against oxidant stresses, and it can be anticipated that the non-toxic lipid A derivatives will have these beneficial effects as well.

The lipid A derivatives of the present invention are preferably introduced into the circulation of an animal by intravenous, intraperitoneal or intramuscular routes, and appear to induce a state of relative resistance to the deleterious effect of LPS. When thus employed, the compounds may be administered in the form of parenteral solutions containing the selected protective compound in a sterile liquid suitable for intravenous or other administration. There also may be indications for which the lipid A derivatives are best administered orally or topically. When intended for such indications the compounds may be combined with pharmaceutical deluents and the like and formed into dosage form suitable for oral application, such as capsules or tablets, or topical application, such as patches or ointments. The exact route, dose, and administration interval of the selected compound will vary with the size and weight of the animal, and the species, and the desired level of protection.

Table VII

Pet animal and livestock endotoxemias and other pathophysiological entities with high probability of being prevented or treated by administration of the non-toxic derivatives of lipid A of the present invention are the following:
Mammalian Gastritis
Digestive disorders of the rumen including—
  Bloat
  Simple indigestion
  Grain overload
Abomasal disorders
Displacement/torsion of the abomasum Impaction of the abomasum
Edema disease of swine
Colibacillosis of weaned pigs
Enteritis of small and large animals
Small intestinal obstruction
Colon impaction of small animals
Intussuceptions
Intestinal torsion and volvulus
Impaction of the large intestine
Intestinal foreign bodies
Intestinal incarceration
Colitis
Colic in horses
Salmonellosis/typhoid fever
Colibacillosis
Diarrhea of newborn animals
Chronic diarrhea
Toxicosis of chemical and plant origins
Gasrotroinestinal parasites including coccidosis and sareosporidiosis
Malabosorbtion syndrome
Hemorrhagic bowel syndrome
All other syndromes which cause loss of gastrointestinal hemogeneity such as abrupt changes in diet or feeding regimen in mammalian species.
Infectious necrotic hepatitis
Bacillary hemoglobinuria
Hepatitis of parasitic etiology
Hepatic distomatosis
Chemical hepatosis from protein deficiences, vitamin E deficiency, pyrrolizidine alkaloids, from parasites during migrations, infectious and pyrogenic, diseases, metabolic diseases, copper poisonings.
Avian syndromes
Enteritis of infectious or nutritional origin; infectious etiology is intended to include bacterial, viral and parasitic etiologies. Hepatitis of infectious or parasitic etiologies Coccidiosis, hexamitiasis, histomoniasis Human diseases with high probability of being prevented or treated by the administration of the non-toxic lipid A derivatives of the present invention are the following:
  (1) Gram negative sepsis
  (2) Endotoxemia from burn wounds, pyelonephritis, peritonitis, cellulitis, abscess, prostatitis, genitourinary tract infections, mastitis, pneumonia, empyema, cholecystitis, bacterial hepatitis, meningococcemia, gonococcemia, colitis, toxic megacolon, etc.
  (3) Loss of G.I. mucosal barrier, e.g. trauma, druginduced mucositis.

Other possible uses include:
  (1) Use as an LPS antagonist in cell lines with studies evaluating receptor action.
  (2) Use as adjuvants.
  (3) Use for tumor regression.
  (4) The inactivation of suppressor T cells.

REFERENCES

1. Appelmelk, A. J., A. M. J. J. Verweij-Van Vught, D. M. MacLaren, and L. G. Thijs. 1985. An enzyme-linked immunosorbent assay (ELISA) for the measurement of antibodies to different parts of the Gram negative lipopolysaccharide core region. J. Immunol. Methods 82:199–207.
2. Bauss, F., W. Droge, and D. N. Mannel. 1987. Tumot necrosis factor mediates endotoxic effects in mice. Infect. Immun. 55:1622–1625.
3. Beutler, B., N. Krochin, I. W. Milsark, C. Luedke, and A. Cerami. 1986. Control of cachectin (tumor necrosis factor) synthesis: mechanism of endotoxin resistance. Science 222:977–980.
4. Beutler, B., J. Mahoney, N. LeTrang, P. Pekala, and A. Cerami. 1985. Purification of cachectin, a lipoprotein lipases-suppressing hormone secreted by endotoxininduced RAW 264.7 cells. J. Exp. Med. 161:984–995.
5. Beutler, B., I. W. Milsark, and A. Cerami. 1985. Passive immunization against cachectin/tumor necrosis factor protects mice from lethal effect of endotoxin. Science 229:869–871.
6. Danner, R. L., K. A. Joiner, and J. E. Parrillo. 1987. Inhibition of endotoxin-induced priming of human neutrophils of lipid X and aza-lipid X. J. Clin. Invest. 80:605–612.
7. Freudenberg, M. A., D. Keppler, and C. Galanos. 1986. Requirement for lipopolysaccharide-responsive macrophages in galactosamine-induced sensitization to endotoxin. Infect. Immun. 51:891–895.
8. Gifford, G. E., and M. L. Lohmann-Matthes. 1986. Requirement for the continued presence of lipopolysacchatide for production of tumor nectosis factor by thioglycollate-induced peritoneal murine machrophages. Int. J. Cancer 38:135–137.
9. Imoto, M., S. Kusumoto, T. Shiba, E. Th. Rietschel, C. Galanos, and O. Luderitz. 1985. Chemical structure of *Escherichia coli* lipid A. Tetrahedron Lett. 26:907–908.
10. Lehman, V. M., M. A. Freudenberg, and C. Galanos. 1987. Lethal toxicity of lipopolysaccharide and tumor necrosis factor in normal and D-galactosamine-treated mice. J. Exp. Med. 165:657–663.
11. Morrison, D. C. 1983. Bacterial endotoxins and pathogenesis. Rev. Infect. Dis. 5:S733–S747.
12. Pohlman, T. H., R. S. Munford, and J. M. Harlan. 1987. Deacylated lipopolysaccharide inhibits neutrophil adherence to endothelium induced by lipopolysaccharide in vitro. J. Exp. Med. 165:1393–1402.
13. Proctor, R. A., J. A. Will, K. E. Burhop, and C. R. H. Raetz. 1986. Protection of mice against lethal endotoxemia by a lipid A precursor. Infect. Immun. 52:905–907.
14. Qureshi, N., J. P. Honovich, H. Hara, R. J. Cotter, and K. Takayama. 1988. Location of fatty acids in lipid A obtained from lipopolysaccharide of *Rhodopseudomonas sphaeroides* ATCC 17023. J. Biol. Chem. 263:5502–5504.
15. Qureshi, N., K. Takayama, P. Mascagni, J. Honovich, R. Wong, and R. J. Cotter. 1988. Complete structural determination of lipopolysaccharide obtained from deep rough mutant of *Escherichia coli*. Purification by high performance liquid chromatography and direct analysis by plasma desorption mass spectrometry. J. Biol. Chem. 263:11971–11976.
16. Raschke, W. C., S. Baird, P. Ralph, and I. Nakoinz. 1978. Functional macrophage cell lines transformed by Abelson leukemia virus. Cell 15:261–269.
17. Remick, D. G., J. Larrick, and S. L. Kunkel. 1986. Tumor necrosis factor-induced alterations in circulating leukocyte populations. Biochem. Biophys. Res. Commun. 141:818-824.
18. Salimath, P. V., R. N. Tharanathan, J. Wechesser, and H. Mayer. 1983. Structural studies on the nontoxic lipid A from *Rhodopseudomonas sphaeroides* ATCC 17023. Eur. J. Biochem. 136:195-200.
19. Salimath, P. V., R. N. Tharanathan, J. Weckesser, and H. Mayer. 1984. The structure of the polysaccharide moiety of *Rhodopseudomonas sphaeroides* ATCC 17023 lipopolysaccharide. Eur. J. Biochem. 144:227-232.
20. Strain, S. M., I. M. Armitage, L. Anderson, K. Takayama, N. Qureshi, and C. R. H. Raetz. 1985. Location of polar substituents and fatty acyl chains on lipid A precursors from a 3-deoxy-D-manno-octulosinic acid-deficient mutant of *Salmonella typhimurium*. Studies by $^1H$, $^{13}C$, and $^{31}p$ nuclear magnetic resonance, J. Biol. Chem. 260:16089-16098.
21. Strittmatter, R., R. Weckesser, P. V. Salimath, and C. Galanos, 1983, Nontoxic lipopolysaccharide from *Rhodopseudomonas sphaeroides* ATCC 17023. J. Bacteriol, 155:153-158.
22. Takayama, K., and Qureshi, N. 1986. Structures of lipid A, its precursors, and derivatives, p. 5-9, In L. Leive (ed.), Microbiology-1986. American Society for Microbiology, Washington, D.C.
23. Takayama, K., N. Qureshi, and P. Mascagni. 1983. Complete structure of lipid A obtained from the lipopolysaccharides of the heptoseless mutant of *Salmonella typhimurium*. J. Biol. Chem. 258:12801-12803.
24. Takayama, K., N. Qureshi, P. Mascagni, M. A. Nashed, L. Anderson, and C. R. H. Raetz. 1983. Fatty acid derivatives of glucosamine-1-phosphate in *Escherichia coli* and their relation to lipid A. Complete structure of a diacyl GlcN-1-P found in a phosphatidylglycerol-deficient mutant. J. Biol. Chem. 258:7379-7385.
25. Takayama, K., N. Qureshi, E. Ribi, and J. L. Cantrell. 1984. Separation and characterization of toxic and nontoxic forms of lipid A. Rev. Infect. Dis. 6:439-443.
26. Tracy, K. J., B. Beutler, S. F. Lowry, J. Merryweather, E. Wolpe, I. W. Milsark, R. J. Haririr, T. J. Fahey Iii, A. Zentella, J. D. Albert, G. T. Shires, and A. Cerami. 1986. Shock and tissue injury induced by recominant human cachectin. Science 234:470-474.
27. Omar, A. S., Flammann, H. T., Borowiak, D. and Weckesser, J. 1983. Liposaccharides of two strains of the phototropic bacterium Rhodopseudomonas Capsulata, Arch. Microbiol. 134:212-216.
28. Westphal, O., Liideritz, O., Bester, F. (1952) liberdie Extraktion von Bakterier mit Phenol/Wasser. Z. Naturforsch 7b:148-155.
29. Imoto, M., Yoshimura, H., Yamamoto, M., Shimamoto, T., Kusumoto, S., and Shiba, T. (1984) Chemical synthesis of phosphorylated tetra-acyl disacchoride corresponding to a biosynthetic precursor of lipid A. Tetrahedron Lett. 25, 2667-2670.
30. Imoto, M., Yoshimura, H., Sakaguchi, N., Kusumoto, S., and Shiba, T. (1985) Total synthesis of *Escherichia coli* lipid A. Tetrahedron Lett. 26, 1545-1548.
31. Kusumoto, S., Yamamoto, M., and Shiba, T. (1984). Chemical synthesis of lipid X and lipid Y, acyl glucosamine 1-phosphate isolated from *Excherichia coli* mutants. Tetrahedron Lett. 25, 3727-3730.
32. Lederer, J. A., and Czuprynki, C. J. Purification of bovine interleukin from LPS stimulated monocytes. Vet. Immumol. (in press).
33. M. S. 1981. Peritoneal mononuclear phagocytes from small animals in Methods for studying mononuclear phagocytes. Editor D. O. Adams, P. J. Edelson and H. Koren Academic Press New York 1981.
34. Qureshi, N., Mascagni, P., Ribi, E., and Takayama, K. (1985) J. Biol. Chem. 260, 5271-5278.
35. Lederer, J. A., Czuprynski Vet. Immumol. (in press).
36. Meltzer, M. S. (1981) Methods for studying mononuclear phagocytes (Adams, D. O., Edelson, P. J. and Koren, H. eds), Academic Press, New York 63-68.

We claim:

1. A method of treating a mammal to protect said mammal from the toxic effects of Gram-negative endotoxin, said method comprising administering to said mammal a safe and effective amount to protect against said toxic effects of a compound having the following structural formula:

Formula I

[Chemical structure showing disaccharide with substituents $R_1$, $R_2$, $R_3$, $R_4$, $R_9$, $R_{10}$, X, Y and NH groups]

in which X is hydrogen or $$-O-\underset{\underset{O-R_6}{|}}{\overset{\overset{O-R_5}{|}}{P}}\!\!\rightarrow\!O$$

and Y is hydrogen or $$-O-\underset{\underset{O-R_8}{|}}{\overset{\overset{O-R_7}{|}}{P}}-O\,.$$

and both X and Y are not hydrogen; $R_1$ is selected from 2-hydroxy fatty acyl, fatty acyl, keto fatty acyl, unsaturated fatty acyl and branched fatty acyl; $R_3$ is $$CH_3(CH_2)_n-\overset{\overset{OH}{|}}{CH}-CH_2-\overset{\overset{O}{\|}}{C}-;$$

$R_2$ and $R_4$ are the same or different and are hydrogen, $$CH_3(CH_2)_n-\overset{\overset{OH}{|}}{CH}-CH_2-\overset{\overset{O}{\|}}{C}-CH_3(CH_2)_m-\overset{\overset{O}{\|}}{C}-,$$

$$CH_3(CH_2)_n-\overset{\overset{O}{\|}}{C}-CH_2-\overset{\overset{O}{\|}}{C}-$$

$$CH_3(CH_2)_m-\overset{\overset{O}{\|}}{C}-O\atop{\phantom{CH_3(CH_2)_m}}CH_3-(CH_2)_n-\overset{|}{CH}-CH_2-\overset{\overset{O}{\|}}{C}-,$$

alkyl branched or 2-hydroxy fatty acyl group; $R_5$, $R_6$, $R_7$ and $R_8$ are the same or different and are selected from hydrogen, a lower alkyl of 1 to 6 carbon atoms, an aryl, or

in which R is a lower alkyl of 1 to 6 carbon atoms; or a basic group that does not interfere with or detract from the ability of the compound to protect said mammal from the toxic effects of Gram-negative endotoxin desired of the product; $R_9$ and $R_{10}$ are selected from a lower alkyl of 1 to 16 carbon atoms in an ether linkage, a $C_2$ to $C_{18}$ fatty acyl group in an ester linkage or a glycosidic residue having from 1 to 20 glycosidic units per residue n is 1 to 14, but not 10; and m is 2 to 16, but not 12.

2. A compound having the following structural formula:

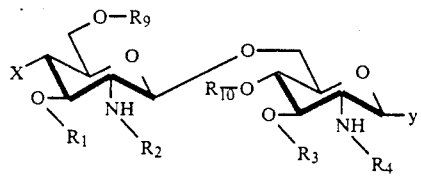

Formula I in which X is hydrogen or

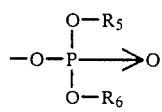

and Y is hydrogen or

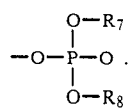

and both X and Y are not hydrogen; $R_1$ is selected from 2-hydroxy fatty acyl, fatty acyl, keto fatty acyl, unsaturated fatty acyl and branched fatty acyl; $R_3$ is

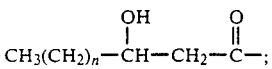

$R_2$ and $R_4$ are the same or different and are hydrogen,

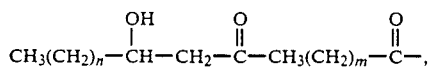

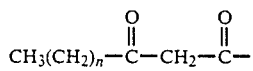

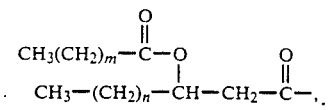

alkyl branched or 2-hydroxy fatty acyl group; $R_5$, $R_6$, $R_7$ and $R_8$ are the same or different and are selected from hydrogen, a lower alkyl of 1 to 6 carbon atoms, an aryl, or

in which R is a lower alkyl of 1 to 6 carbon atoms; or a basic group that does not interfere with or detract from the ability of the compound to protect said mammal from the toxic effects of Gram-negative endotoxin desired of the product; $R_9$ and $R_{10}$ are selected from a lower alkyl of 1 to 16 carbon atoms in an ether linkage, a $C_2$ to $C_{18}$ fatty acyl group in an ester linkage or a glycosidic residue having from 1 to 20 glycosidic units per residue, n is 1 to 14, but not 10; and m is 2 to 16, but not 12; and the compound is not the pentaacyl DPLA from *Rhodopsuedomonas capsulata*.

3. A pharmaceutical composition for administration to a mammal to protect said mammal from the toxic effects of Gram-negative endotoxin, said composition comprising a compound of Formula I of claim 2 and a pharmaceutical carrier.

* * * * *